(12) United States Patent
Baumann

(10) Patent No.: US 10,209,438 B2
(45) Date of Patent: Feb. 19, 2019

(54) ENDOSCOPE, EXOSCOPE OR MICROSCOPE AND A METHOD FOR ILLUMINATING A MANIPULATION REGION OF AN ENDOSCOPE, EXOSCOPE OR MICROSCOPE

(71) Applicant: Karl Storz SE & Co. KG, Tuttlingen (DE)

(72) Inventor: Harald Baumann, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 813 days.

(21) Appl. No.: 14/559,570

(22) Filed: Dec. 3, 2014

(65) Prior Publication Data

US 2015/0185414 A1    Jul. 2, 2015

(30) Foreign Application Priority Data

Dec. 5, 2013 (DE) .................. 10 2013 113 511

(51) Int. Cl.
*G02B 6/04* (2006.01)
*A61B 1/07* (2006.01)
(Continued)

(52) U.S. Cl.
CPC ............ *G02B 6/04* (2013.01); *A61B 1/00006* (2013.01); *A61B 1/00057* (2013.01);
(Continued)

(58) Field of Classification Search
CPC ... A61B 1/0615; A61B 1/0623; A61B 1/0638; A61B 1/0669; A61B 1/07;
(Continued)

(56) References Cited

U.S. PATENT DOCUMENTS 6,524,237 B1 * 2/2003 McGowan ............... G02B 6/04
  348/E7.087
2003/0219207 A1 * 11/2003 Guy .......................... A61B 1/07
  385/49

(Continued)

FOREIGN PATENT DOCUMENTS

DE          1113788 B      9/1961
DE         29812048 U1    11/1998
(Continued)

*Primary Examiner* — John P Leubecker
*Assistant Examiner* — Genja Frankert
(74) *Attorney, Agent, or Firm* — Whitmyer IP Group LLC

(57) ABSTRACT

An endoscope, exoscope or microscope, including an optical fiber bundle for transmitting light from the proximal end to the distal end, the optical fiber bundle showing a contiguous bundle at the proximal end and a plurality of partial bundles or else individual fibers at the distal end. Furthermore, it shows a light source for coupling light into the one proximal end of the optical fiber bundle and including a multiplicity of individually actuatable individual-light sources arranged in an array-like manner, and a control unit for actuating the individual-light sources using an assignment function which represents the assignment of a proximal fiber end to a partial bundle. Here, the proximal ends of the fibers which are assigned to one partial bundle are arranged on a surface in such a way that proximal ends of fibers assigned to a different partial bundle are arranged therebetween.

19 Claims, 2 Drawing Sheets

(51) Int. Cl.
*A61B 1/00* (2006.01)
*A61B 1/06* (2006.01)
*G02B 6/42* (2006.01)
*G02B 23/24* (2006.01)
*G02B 21/06* (2006.01)

(52) U.S. Cl.
CPC ........ *A61B 1/00167* (2013.01); *A61B 1/0669* (2013.01); *A61B 1/0684* (2013.01); *A61B 1/07* (2013.01); *G02B 6/4202* (2013.01); *G02B 6/4204* (2013.01); *G02B 23/2469* (2013.01); *A61B 1/00059* (2013.01); *G02B 21/06* (2013.01)

(58) Field of Classification Search
CPC ............ A61B 1/00006; A61B 1/00167; A61B 1/0684; A61B 1/00057; A61B 1/00059; A61B 1/00096; A61B 1/0676; G02B 6/04; G02B 6/4204; G02B 23/2469; G02B 6/4202; G02B 21/06; G01N 21/8806
See application file for complete search history.

(56) References Cited

U.S. PATENT DOCUMENTS

| | | | |
|---|---|---|---|
| 2005/0140270 A1 | 6/2005 | Henson et al. | |
| 2005/0267328 A1* | 12/2005 | Blumzvig | A61B 1/00096 600/109 |
| 2005/0276553 A1* | 12/2005 | Kazakevich | A61B 1/0607 385/115 |
| 2006/0171693 A1 | 8/2006 | Todd et al. | |
| 2009/0116260 A1* | 5/2009 | Rovegno | A61B 1/00052 362/555 |
| 2010/0182405 A1* | 7/2010 | Monteiro | G02B 6/04 348/45 |
| 2011/0001431 A1* | 1/2011 | Brukilacchio | F21K 9/00 315/152 |
| 2011/0257483 A1 | 10/2011 | Mizuyoshi et al. | |
| 2015/0241634 A1* | 8/2015 | Coutard | A61B 5/0071 600/317 |

FOREIGN PATENT DOCUMENTS

| | | |
|---|---|---|
| DE | 10001289 C1 | 10/2001 |
| DE | 102007063262 A1 | 6/2009 |
| DE | 102008033506 A1 | 1/2010 |
| DE | 102010013307 A1 | 9/2011 |
| DE | 102010033427 A1 | 2/2012 |
| DE | 102010054666 A1 | 6/2012 |
| DE | 102011054031 A1 | 10/2012 |
| EP | 2263519 A2 | 12/2010 |
| EP | 2446810 A1 | 5/2012 |
| GB | 2339926 A | 2/2000 |
| JP | 2002102163 A | 4/2002 |
| WO | 0123913 A2 | 4/2001 |

* cited by examiner

|   | A | B | C | D | E | F |
|---|---|---|---|---|---|---|
| a | 1 | 2 | 4 | 1 | 3 | 2 |
| b | 4 | 3 | 1 | 2 | 1 | 0 |
| c | 3 | 1 | 3 | 4 | 2 | 3 |
| d | 4 | 3 | 2 | 3 | 3 | 4 |
| e | 2 | 2 | 4 | 2 | 1 | 2 |
| f | 1 | 2 | 1 | 4 | 4 | 3 |
| g | 3 | 1 | 3 | 1 | 2 | 2 |
| h | 2 | 4 | 2 | 2 | 4 | 3 |
| i | 2 | 1 | 1 | 3 | 1 | 1 |
| j | 4 | 3 | 4 | 2 | 2 | 2 |
| k | 1 | 4 | 1 | 3 | 3 | 4 |
| l | 3 | 3 | 2 | 4 | 2 | 3 |

ENDOSCOPE, EXOSCOPE OR MICROSCOPE AND A METHOD FOR ILLUMINATING A MANIPULATION REGION OF AN ENDOSCOPE, EXOSCOPE OR MICROSCOPE

FIELD OF THE INVENTION

The invention relates to an endoscope, exoscope or microscope and also to a method for illuminating a manipulation region of an endoscope, exoscope or microscope and also to a method for determining an assignment function for an endoscope, exoscope or microscope.

BACKGROUND OF THE INVENTION

The German patent DE 1113788 B has disclosed an endoscope showing a detached light source, the light of which is coupled into the endoscope by means of an optical waveguide and guided from the proximal end of the endoscope comprising the eyepiece to the distal end of the endoscope. Here, the endoscope is typically situated in a body cavity and emits the supplied light at said location in a substantially single direction for the purposes of illuminating the body cavity. The significant heat generated by the detached light source cannot lead to the patient being harmed as a result of the detached light source. Furthermore, the handling of this endoscope was found to be comfortable since the waste heat of the light source does not lead to significant heating of the endoscope.

The laid-open application DE 10 2011 054 031 A1 has disclosed an exoscope which serves for observing and illuminating an object field on a patient from a location away from the body of the patient. By means of a detached light source, the light for illumination purposes is supplied to the exoscope by means of an optical fibre cable and transmitted within the exoscope to the distal end comprising the head part with the aid of optical fibres and used at said location for illuminating the object field. Here, there are two exit openings for the light at the head, into which openings two partial bundles of the optical fibre bundle arranged in the exoscope open.

DE 10 2007 063 262 A1 has disclosed an illumination device for generating light for endoscopy or microscopy. In order to avoid the problems of the heating of the light source including an array of LEDs, said illumination device shows a plurality of cooling devices using heat pipes. This cooling was found to be very complicated.

Endoscopes with a variable, adjustable viewing direction are known from EP 2 263 519 A2 and EP 2 446 810 A1. These endoscopes require a precisely adjusted illumination of the region in which, depending on the set viewing direction, viewing takes place. Here, two options are presented. Firstly, there is large-scale illumination of the whole possible viewing region. Secondly, it is suggested to select not only the viewing direction in a selective manner but also to additionally adapt the illumination direction in a selective manner and parallel thereto by virtue of an optical waveguide at the distal end of the endoscope also being swiveled therewith and the illumination direction being modified thereby. This solution was found to be very complicated mechanically and requires a significant volume in the region of the distal end, significantly restricting the introduction of such a variable illumination into endoscopes with a small tube diameter. The problem of the heat load in the region of the light source clearly emerges in the case of the large-scale illumination.

Furthermore, the US patent application US 2006/0171693 A1 discloses an endoscope which includes a plurality of light sources, separated from one another, in the handle thereof, which light sources are respectively connected to a dedicated optical fibre bundle and respectively couple the generated light directly into the respectively assigned optical fibre bundle. Each optical fibre bundle subsequently transmits the light to the distal end thereof. At the distal end of the endoscope, the distal ends of the optical fibre bundles, respectively in a separate manner, open into spaced apart surfaces for decoupling the light. The optical fibre bundles with the surfaces for decoupling are arranged uniformly around the central image transmission channel and radiate in parallel in the same direction at the distal end. This endoscope shows a very complicated design.

SUMMARY OF THE INVENTION

The present invention is based on the object of developing an endoscope, exoscope or microscope which, while having a simple design, provides the option of selectively illuminating individual regions of the manipulation field of the endoscope and which, in the process, shows efficient energy or heat management. A further object of the present invention consists of specifying a corresponding method for illuminating a manipulation region of an endoscope, exoscope or microscope, which shows the corresponding advantages. Moreover, the invention is based on the object of specifying a method for determining an assignment function for an endoscope, exoscope or microscope.

These objects according to the invention are respectively achieved by an endoscope, exoscope or microscope and by a method for determining an assignment function and by a method for illuminating a manipulation region of an endoscope, exoscope or microscope.

The endoscope, exoscope or microscope according to the invention shows an optical fibre bundle for transmitting light from the proximal end to the distal end, wherein a contiguous bundle of optical fibres is present at the proximal end while a plurality of partial bundles which are separated from one another are formed at the distal end of the optical fibre bundle. In an extreme case, individual fibres or distal fibre ends can be referred to as partial bundles.

The light source consists of a multiplicity of individually actuatable individual-light sources arranged in an array-like manner and enables the generated light to be coupled into the proximal end of the optical fibre bundle. According to the invention, the control unit for actuating the light source is embodied in such a way that it is suitable for selectively actuating the individual-light sources and it enables this in such a way that it activates or deactivates, or controls the brightness of, individual selective light sources of the array-shaped light source using an assignment function which, for example, is stored in the form of an assignment table. The assignment of a proximal fibre end to a specific partial bundle is stored in the assignment function. According to the invention, this renders it possible to selectively illuminate the proximal fibre ends with the aid of the individual-light sources assigned to this fibre end, which fibre ends transmit the light thereof to a desired partial bundle and therefore do not impinge other unwanted partial bundles with light. Here, the proximal ends of the fibres, which are assigned to a partial bundle, are arranged on a surface of the array-shaped light source in such a way that other fibres assigned to a different partial bundle are arranged between the proximal ends thereof. This is connected with an arbitrary distribution or guidance of the optical fibres in the optical fibre bundle.

The assignment function renders it possible to activate individual-light sources of the array, which are distributed over a large area, together such that the light thereof into the proximal ends of the optical fibres assigned to the individual-light sources, which proximal ends of the optical fibres are connected to one or more specific partial bundles, such that coupled-in light only emerges from these specific partial bundles. This firstly enables a selective light emission via selected, specific partial bundles and secondly provides a distribution of the individual-light sources over a relatively large area of the array-shaped light source such that the local heating in the array of the light source is restricted despite the high integration density of the individual-light sources and, as a result, the service life of the individual-light sources is significantly increased. Therefore, the assignment function firstly represents an assignment of the proximal fibre ends to a specific partial bundle, and also, simultaneously, an assignment of the individual-light sources of the array-shaped light source to a specific partial bundle or, in the extreme case, to a specific individual fibre. The cause of this is that the individual-light sources are specifically assigned to individual proximal fibre ends.

Preferably, each single individual-light source is assigned to an individual fibre end here in such a way that the emitted light is only coupled into the latter. Those light sources which in terms of their size and emission direction enable coupling into one or, in particular, a single optical fibre end and which can in the process be actuated selectively with the aid of an appropriate control unit are particularly suitable as a light source with a multiplicity of individual-light sources arranged in an array-shaped manner. At the same time, a plurality of individual-light sources distributed over a relatively large area, which does not necessarily comprise the complete array surface, can, according to the invention, be activated in such a way that they selectively couple light into the optical fibre bundle in accordance with the assignment function such that only the desired partial bundle at the distal end emits light. Here, small deviations of the order of percent when coupling light into other, unwanted fibre ends, which are connected to other, unwanted partial bundles, are harmless as long as the number of the used unwanted optical fibres lies in the order of a few percent of the used wanted fibres in accordance with the assignment function. The light transmitted by the used unwanted fibres leads to little background light in the manipulation field, which typically is not bothersome, and moreover does not lead to significant additional heating in the endoscope, exoscope or microscope.

The method according to the invention for illuminating a manipulation region of an endoscope, exoscope or microscope is distinguished by virtue of the light being transmitted from the proximal end of the endoscope to the distal end by means of an optical fibre bundle, wherein a single contiguous bundle is provided at the proximal end of the optical fibre bundle while a plurality of mutually separated partial bundles are provided at the distal end of the optical fibre bundle, which partial bundles, in particular, point in different directions. This is of particular interest, precisely for an endoscope, exoscope or microscope with a variable viewing direction.

The array-shaped light source according to the invention consists of a multiplicity of individually actuatable individual-light sources, which, in a selectively activated manner, couple light into selective proximal fibre ends of individual optical fibres assigned to the individual-light source. The individually actuatable individual-light sources of the light source are actuated by the control unit according to the invention by means of a predetermined assignment function representing the assignment of a proximal fibre end of the optical fibre bundle to a partial bundle in such a way that only those individual-light sources which are assigned to a specific wanted partial bundle are activated. As a result, it is possible to selectively activate the individual-light sources, which are distributed at a distance from one another over the array-shaped light source in a large-scale manner, and hence possible to activate said individual-light sources as a function of the assignment function which, in particular, can be realized in the form of an assignment table, and thereby achieve a selective light emission via one or a few partial bundles. This provides a particularly heat and energy efficient method for illuminating the manipulation region of an endoscope, exoscope or microscope.

Additionally, the invention also relates to a method for determining an assignment function for an endoscope, exoscope or microscope as described above. Here, all or some of the individual-light sources arranged in an array-shaped manner are selectively activated, in particular in a sequential manner, and at least one optical detector, which may be realized by means of e.g. a camera or a simple photo-sensor or a photodiode, is used to log which one of the various partial bundles at the distal end of the optical fibre bundle emits light. Using this, an assignment of individual individual-light sources, and hence of individual proximal fibre ends, to individual partial bundles is determined, and logged and stored in an assignment function, in particular as an assignment table. Hence this assignment function is available, in particular in the form of an assignment table, for actuating individual-light sources of an array-shaped light source of an endoscope, exoscope or microscope according to the invention. As a result, it is possible to activate individual individual-light sources in a targeted manner on the basis of the information in the assignment function and thereby use e.g. a single partial bundle for illuminating the manipulation region of an endoscope, exoscope or microscope in such a way that light is only emitted therefrom. As a result of this simple way of determining an assignment function, the latter can be reliably determined, logged and stored such that the advantageous implementation of the invention in the form of an endoscope, exoscope or microscope according to the invention or in the form of a method for illuminating such an endoscope, exoscope or microscope is advantageously made possible.

According to a preferred embodiment of the method according to the invention, the identity of the light source and/or the position of the light source in relation to the proximal end of the optical fibre bundle is logged and a suitable assignment function is selected as a function thereof from a memory assigned to the control apparatus and used for actuating the individual, selectively actuatable individual-light sources of the light source as required. Here, according to the invention, various assignment functions which relate to different situations of the endoscope, exoscope or microscope according to the invention, are stored in a memory. Said situations are determined by the use of different light sources, or else by different positions or orientations of the light source in relation to the proximal end of the fibre bundle, be it in the form of an alternative selection or in the form of a cumulative implementation. Depending on the selection of the used light source, and hence on the identity thereof, it is possible to use the respectively fitting assignment function, in particular in the form of an assignment table, which light source is preferably implemented as an internal light source in the handle or else as an external light source and can therefore easily be adapted to the different fields of application of the endoscope, exoscope or microscope or else can be replaced within the scope of servicing. Here, the fitting assignment function was established at an earlier time and stored in a memory for the assignment function of the endoscope, exoscope or microscope. For an external light source, care has to be taken that the cable is applied in a manner secured against twisting and that the actuation function is adapted to the respective cable.

In a corresponding manner, it is also important that the assignment function is selected in a manner fitting to the used position of the light source in relation to the proximal end of the optical fibre bundle, as well as in view of the orientation, the alignment or the lateral offset.

In addition to the option of storing a multiplicity of assignment functions in a memory for different positions, it is also possible to calculate the associated assignment functions from a base assignment function from the relative position data in relation to one another, in particular from the offset, the alignment or the orientation in relation to one another, after logging the positioning of the light exit surface of the optical fibre cable in relation to the proximal end surface of the optical fibre bundle and it is also possible to use the calculated assignment function by means of the control unit. Here, the assignment functions can be determined according to simple mathematical relationships, the for modified new position function, from a base assignment function, which corresponds to the assignment function at a predetermined position, determined in advance, particularly in the case of a lateral offset, but also in the case of a modified orientation or alignment. The effects of a lateral offset, of a modified orientation or of a modified alignment can be represented by mathematical, physical mapping models. Using this, it is possible to determine a multiplicity of assignment functions from a specific base assignment function, depending on the offset, the orientation or the alignment, and it is possible to use these for the operation of the endoscope, exoscope or microscope. Hence, the storage space can be limited or the determination outlay for the assignment function by measuring can be significantly restricted.

It has particularly proven its worth to realize the light source from a multiplicity of LEDs, semiconductor lasers or optical waveguide fibres, wherein use is preferably made of only LEDs, semiconductor lasers or optical waveguide fibres. Additionally, a combination of these possible individual-light sources is also possible.

As a result of the new development in the miniaturization of the LEDs, these show, in terms of the lateral extent thereof, the same size as the cross sections of the optical waveguide fibres. Currently, semiconductor lasers are slightly larger. By using miniaturized LEDs or optical waveguide fibres, it is possible to generate a very compact, small area light source, which is suitable to be connected directly to the end surface of the optical fibre bundle and in the process ensures a good reliable assignment between individual-light source and one end of an optical waveguide fibre. This is provided to a particular extent if the form and/or the size of the fibre end at the proximal end of the optical fibre bundle corresponds to, in particular equals, the form and/or the size of the assigned individual-light source. Particularly if the latter is selected to be the same both in respect of the form and also in respect of the size, it is possible to set an optimized 1:1 assignment and hence a very reliable assignment function and it is also possible to use it subsequently for controlling the individual-light sources of the endoscope, exoscope or microscope respectively. As an alternative to the size or form selected to be the same, it has also proven its worth to select the individual-light sources in such a way that they are selected to be smaller in terms of size or selected in terms of form in such a way that they come to rest within the area of the fibre end of the associated optical fibre and therefore substantially only emit light into the one assigned fibre. Here, it was also found that certain lateral emissions of the individual-light sources into other, adjacent optical fibres are harmless as long as the predominant part of the emitted radiation is coupled into the wanted optical fibre. In particular, it has proven its worth for less than a specific component, e.g. 20%, of the emitted radiation to be coupled into different, unwanted fibres.

By providing miniaturized LEDs or optical waveguide fibres, it is possible to ensure particularly efficient coupling of the light source to the proximal end of the optical fibre bundle, without there being significant losses or pronounced cases of incorrect coupling-in.

It has particularly proven its worth to select the form and the size of the proximal end of the optical fibre bundle in such a way that it corresponds or is equal to the form and/or the size of the light source. This renders it possible to ensure reliable efficient coupling of the light of the array-shaped light source into the end of the optical fibre bundle.

In addition to the particularly preferred option of the emitted light of the individual-light sources being coupled directly into a single or a few individual optical fibres and of thereby keeping possible losses low, it has alternatively proven its worth to arrange one or more optical units for focussed coupling of the emitted light into the fibres between the individual-light sources of the light source and the proximal end of the optical fibre bundle.

Here, provision is preferably made for a common optical unit for the individual-light sources, by means of which it is possible to realize a large-scale array made of individual-light sources, e.g. of LEDs, and to image the individual-light sources onto the proximal end surface of the optical fibre bundle with the aid of a single optical unit in such a way that there is an unambiguous assignment from a single individual-light source to a fibre end of an individual fibre. Precisely by using an optical unit it becomes possible to reliably image a relatively large array or relatively large individual-light sources through a single simple optical arrangement to a restricted proximal end surface of the fibre bundle.

Alternatively, it is also possible to assign selective optical units to individual individual-light sources or to a plurality of adjacent individual-light sources in such a way that the light emitted thereby is imaged selectively on a single end surface of an optical fibre and thus coupled into the latter. As a result of this, a multiplicity of individual optical units with a very small diameter need to be fixed in a precise position; this is rendered possible by the use of chip technologies. It is also suitable to use components such as micromechanical mirrors (MEMS, DMD) for the targeted deflection of the emitted light in the direction of a proximal end surface of an optical waveguide fibre predetermined by the assignment function.

As a result of the provision of one or more corresponding optical units, it is possible to increase the light yield of the light source or of the individual-light sources by virtue of these being able to be realized with a large area and by virtue of the spacing of the individual individual-light sources in the array being able to be enlarged, which improves the quality, in particular the reliability, of the array-shaped light source.

It was found to be particularly advantageous to connect the proximal end of the optical fibre bundle to the light source in a positionally secured manner. What this ensures is that the assignment function, suitable for the secured position, can be used permanently. Hence, a simple, safe and reliable, and hence heat and energy efficient, implementation of the endoscope, exoscope or microscope is provided. In addition to the option of providing a positionally secured connection by latching, screwing, riveting or welding, it has particularly proven its worth to adhesively bond the light source to the proximal end of the optical fibre bundle. Here, use is preferably made of an adhesive between the light source and the proximal end of the optical fibre bundle which, as a result of the optical properties thereof, does not have a negative influence, or only a small negative influence, on the coupling of the light from the individual-light source into the assigned fibres. This type of positionally secured connection provides a permanent and easily producible connection. Alternatively, the provision of detachable connections, which are positionally secured in the connected state and, as a result of this, do not change in terms of the positioning, has also proven its worth. As result, it is possible to replace the light source or the optical fibre bundle, which may occur within the scope of servicing services.

A particularly preferred embodiment of the endoscope, exoscope or microscope according to the invention is distinguished by the fact that the light source is arranged in the endoscope, in particular integrated in the handle thereof, and, as a result, there is no need for complicated cabling for supplying light for the purposes of illuminating the manipulation region. This is made possible, in particular, by virtue of the fact that the array-shaped light source is preferably selected to be so small that it corresponds to the proximal end surface of the optical fibre bundle in terms of the size and form thereof and is positioned at only a small distance from the latter. As a result of this preferred embodiment and positioning of the light source in relation to the optical fibre bundle, a very compact arrangement is provided, which can be reliably arranged in e.g. the handle or in a different housing region of the endoscope, exoscope or microscope. Precisely by the large-scale distribution according to the invention of the activated individual-light sources for actuating an individual partial bundle, it is possible to limit the heat load of this very compact light source and integrate the former e.g. in a handle of an endoscope or exoscope, without the latter being heated in an uncomfortable manner.

As an alternative thereto, it has also proven its worth to realize the light source in a manner detached from the remainder of the endoscope, exoscope or microscope, and hence separately from the latter, and to guide the light from the light source by means of an optical fibre cable from the light source to the remainder of the endoscope and couple said light into the proximal end surface of the optical fibre bundle at said location. This arrangement enables the simple interchange of the external light source, for example depending on the field of use of the endoscope, exoscope or microscope, or in the case of damage to the light source. Here, the assignment function is selected in such a way that it takes this interposed optical fibre cable into account. In this case, what is important to the assignment function is, in particular, whether and how the optical fibre cable modifies the position of the optical fibres, into which the light from an individual-light source is coupled, relative to the position during decoupling. This change is to be taken into account in the assignment function. This is achieved, in particular, by virtue of the fact that the external light source with the optical fibre cable is considered to be an overall light source when determining the assignment function. Thus, the unit consisting of light source and optical fibre cable is considered functionally to be a light source, which emits the light at the coupling surface of the optical fibre cable to the endoscope and hence to the proximal end of the optical fibre bundle. In the case of these couplings, means are provided and these set an unambiguous positioning in a defined manner such that the desired fixed positioning is always provided during the assembly, in particular as a result of positive guidance. The provided unambiguous positioning in this case is distinguished, in particular, by a correct lateral positioning of the light exit surface of the optical fibre cable with respect to the proximal end surface of the optical fibre bundle, by a correct relative orientation (relative rotational position) or by the correct alignment (correct tilt of the surfaces in relation to one another). As a result, a reliable selection of the assignment function for the actuation of the individual-light sources is provided.

Alternatively, it has also proven its worth to log the positioning and, cumulatively or alternatively thereto, the used light source of the endoscope, exoscope or microscope according to the invention and to select the suitable assignment function for controlling the light source as a function thereof. In order to identify the light source, it has particularly proven its worth to provide and use encodings of the light source by means of optical and/or electric, in particular electromagnetic, codes. By way of example, the positioning of the light source can be reliably logged with the aid of predetermined markers, in particular optical markers, and taken into account when determining the assignment function. In particular, leading edges which ensure positive guidance into a predetermined position of the light source in relation to the proximal end of the optical fibre bundle have particularly proven their worth as preferred means for unambiguously setting the position of the light source in relation to the proximal end of the optical fibre bundle. This provides very simple and reliable handling of the endoscope, exoscope or microscope according to the invention.

Particularly in the case of an endoscope, exoscope or microscope with a variable viewing direction, it has particularly proven its worth for the partial bundles at the distal end of the endoscope, exoscope or microscope to point into the potential manipulation region in different directions. The assignment function provides the option of selectively using the various partial bundles. As a result the option is provided of enabling a sufficient and safe illumination in the desired viewing direction of the endoscope, exoscope or microscope in a very energy efficient manner and with good heat management, particularly in these medical instruments, and of thereby ensuring safe handling.

Furthermore, the control unit for actuating the light source of a preferred endoscope, exoscope or microscope according to the invention shows the option of actuating the light source with a predetermined illumination profile in such a way that selected regions of the possible illumination region are illuminated with a predetermined intensity. Here, individual regions or assigned individual-light sources are not activated, others are activated in a dimmed manner and others are activated with full power. This significantly increases the field of use of the endoscope, exoscope or microscope according to the invention.

In other words, the invention can be described by an unsorted fibre bundle for transmitting light to a multiple light source, which is embodied as an array, being coupled in an endoscope, exoscope or microscope, wherein, with the aid of an electronic control, individual fibres of different partial bundles are illuminated as selectively as possible by actuating individual, selective individual-light sources of the multiple light source so as only to generate light for a restricted illumination region which is currently being observed.

The actuation of the individual-light sources according to the invention is logged and stored during the assembly by means of a device for determining an assignment function between partial bundles and an individual-light source. This assignment function corresponds to the assignment of the individual partial bundles to the proximal end surfaces of the fibres which are assigned to the respective individual-light sources.

The multiple light source shows a very high integration density of the individual-light sources. The individual-light sources are preferably applied to the same substrate with a minimized separating web. The multiple light source is configured in a manner comparable to a CMOS sensor, in which each pixel is an individual, separately actuatable individual-light source, e.g. in the form of an LED. The control for selective actuation of the individual-light sources as a function of the established assignment function is preferably also arranged on the substrate of the multiple-light source.

This invention was found to be very compact, energy and heat efficient and simple to produce.

In the following text, the invention is described on the basis of individual examples in the figures. The invention is not restricted to these examples.

BRIEF DESCRIPTION OF THE DRAWINGS

In detail.

DETAILED DESCRIPTION OF THE INVENTION

Figure 1:
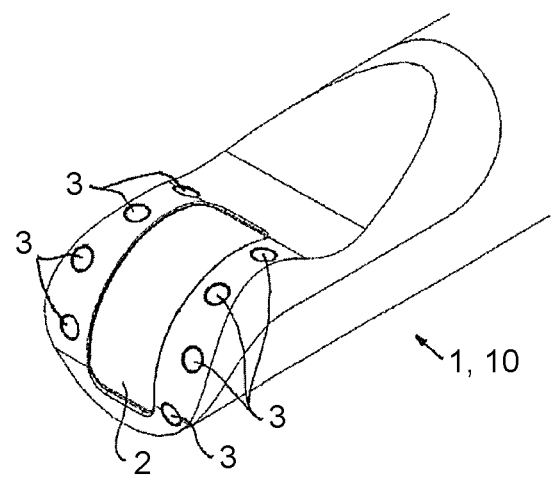
FIG. 1 shows a schematic illustration of an exemplary distal end of an endoscope with a variable viewing direction.

FIG. 1 shows, in an oblique view, the schematic setup of an exemplary distal end 1 of an endoscope 10 according to the invention. In the centre, it is possible to identify the observation window 2, which has an elongate design and is arranged centrally in the region of the distal end 1. Here, the observation window 2 has an arcuate embodiment and shows a substantially rectangular form here, which has a substantially cylindrically arcuate embodiment. Light exit openings 3 are arranged along the longitudinal extent of the observation window 2. Here, this relates to a total of eight light exit openings 3, into which respectively one partial bundle 13 of the optical fibre bundle 11 for transmitting light from the proximal end 2 to the distal end 1 of the endoscope 10 opens. At the distal end 1, the partial bundles 13 are adhesively bonded to one another in the light exit openings 3 in such a way that the light exit openings have a gas- and liquid-tight, and hence autoclavable, design. Here, the partial bundles 13 of the light exit openings 3 point into the manipulation region of the endoscope 10 in different directions. Consequently, the different light exit openings 3 provide the option of illuminating different spatial regions in the manipulation region of the endoscope 10.

Figure 2:
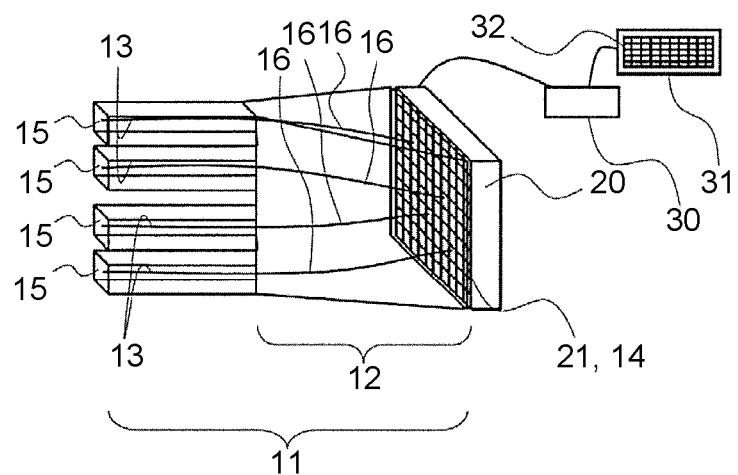
FIG. 2 shows a schematic illustration of an exemplary fibre actuation of an exemplary endoscope.

FIG. 2 depicts a schematic setup of the endoscope 10 and, here, of the optical fibre bundle 11, of the light source 20, of the control unit 30 comprising the associated memory 32.

The light source 20 constitutes a planar, rectangular, array-shaped arrangement of individual-light sources 21. The individual-light sources 21 are arranged in columns and lines in a chequerboard-like manner and form the light source 20. The individual-light sources 21 are realized as superminiaturized LEDs on a common substrate. The size thereof corresponds to the diameter of a typical optical fibre for transmitting light. Each individual-light source 21 can be uniquely defined by stating the column and the line. The control unit 30 is embodied in such a way that it can individually actuate each individual individual-light source 21 of the light source 20 in a selective manner in such a way that said individual-light source is activated and emits light or is deactivated.

In addition to the light source 20 and the control unit 30, the endoscope 10 according to the invention shows an optical fibre bundle 11 which, at the proximal end 14 thereof, shows a single contiguous bundle 12 of optical fibres 16. It is possible to identify four mutually separated partial bundles of different optical fibres 16 at the other distal end 15 of the optical fibre bundle 11. The assignment of the individual optical fibres 16 from the proximal end 14 to the distal end 15 is arbitrary; this means that the fibres extend incoherently from the proximal end 14 to the distal end 15. Hence, the optical fibres 16, which form a common partial bundle 13, do not form a contiguous, compact and well-sorted arrangement of optical fibres at the proximal end 14 of the optical fibre bundle 11, but, according to the invention, are arranged distributed over the end surface of the proximal end 14 of the optical fibre bundle 11. Hence, a varying number of different optical fibres 16 belonging to different partial bundles 13 are arranged in the end surface between the optical fibre ends of the one common partial bundle 13.

Arranged directly adjacent to the proximal end 14 of the optical fibre bundle 11 is the array-shaped light source 20 made of a multiplicity of individual-light sources 21. In terms of their cross section, the individual-light sources 21 are selected in such a way that the emission characteristics thereof correlate with the end surface of an individual optical fibre 16 at the proximal end 14 of the optical fibre bundle 11 in such a way that the emitted light from the individual-light source 21 is largely or completely coupled into the proximal end 14 of the optical fibre 16. There is a 1:1 assignment between the individual-light source 21 and the optical fibre 16. Hence, it is possible by means of selective actuation of the light source 20 with the aid of the control arrangement 30 to activate a predetermined selection of individual-light sources 21 and, with the aid thereof, it is possible to couple light into assigned individual proximal ends 14 of the optical fibres 16, which subsequently transmit the light to the distal end 15 thereof in order to emit it there.

According to the invention, the activated individual-light sources 21 are selected with the aid of the control arrangement 30, which accesses a memory 32 with assignment functions stored therein. The assignment function is realized as an assignment table 31.

If light is to be selectively radiated in a predetermined direction by the endoscope 10, the control arrangement 30 will selectively actuate the individual-light sources 21 in such a way that only said light sources couple light into the proximal ends 14 of the optical waveguide fibres 16 assigned thereto, which proximal ends guide the light into the partial bundle 13 which points into the envisaged, wanted direction. Other partial bundles are not illuminated or only illuminated to a minor extent. The assignment table 31 of the memory 32 sets which individual-light sources 21 represent which partial bundle 13 such that the option of selectively impinging light onto individual partial bundles 13 and accordingly emitting light in the corresponding emission direction is made possible with the aid of the control arrangement 30.

Due to the arbitrary distribution of the optical fibres 16 in the optical fibre bundle 11, and hence due to the arbitrary distribution in the proximal end surface of the proximal ends 14 of the optical fibres 16 assigned to a partial bundle 13, which proximal end surface shows the same distribution of the individual-light sources 21 to be activated in the array-like light source 20, it is possible to distribute the activated individual-light sources 21 over a relatively large area and, as a result thereof, significantly reduce the susceptibility to overheating, which can cause a failure of the individual-light sources 21.

Additionally, the manufacture of the light transmitting components of an endoscope 10 can be significantly simplified by the use of the arbitrarily distributed optical fibres 16 in the optical fibre bundle 11, wherein, however, this is accompanied by an additional required step according to the invention for establishing the assignment function or the assignment table 31, or wherein such a step is necessary. Manufacturing can be significantly simplified in relation to the prior art by the partial dispensation of the sorting of the optical fibres 16 of the optical fibre bundle 11 and the partial dispensation of keeping said optical fibres sorted.

Figures 3, 4:
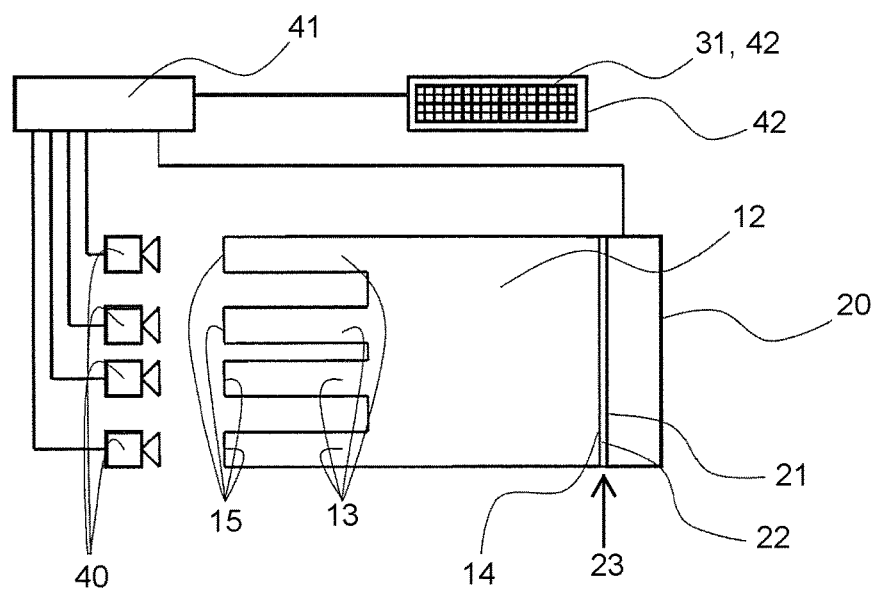
FIG. 3 shows an exemplary assignment table and FIG. 4 shows a schematic arrangement for determining an assignment function.

An exemplary simplified assignment table 31 is depicted in FIG. 3. An element of the table is assigned to each individual-light source 21 of the array-shaped light source 20, wherein the columns A, B, C, D, . . . and lines a, b, c, d, . . . correspond to the arrangement of the individual-light sources 21 in the array-shaped light source 20 on the common substrate. The value in a field of the assignment table 31 corresponds to a unique numbering of the partial bundles 13, which open out at the distal end 1 of the endoscope 10 and which can shine in different directions of the manipulation region in a directed manner.

There are four partial bundles 13 in the example of FIG. 2. Accordingly, the simplified assignment table 31 of FIG. 3 shows fields with the numbers 1, 2, 3, 4, which correspond to the four partial bundles 13 in FIG. 2. If light is to be emitted in the direction of the partial bundle 13 with the number 1, the fields of the assignment table 31 which are provided with the entry 1 are selected in the assignment table 31 in the memory 32. The individual-light sources 21 corresponding to these fields are then activated by means of the control arrangement 30. Other light sources 21 are not activated, and so a set of individual-light sources 21 distributed over a relatively large area is activated and the emitted light is coupled into the directly adjacent end surfaces 14 of the assigned optical fibres 16 and, making use according to the invention of the selective actuation on the basis of the assignment table 31, light only emerges from the partial bundles 13 with the number 1, despite the arbitrarily distributed optical fibres 16. Possible stray light which couples into other fibres typically only leads to diffuse background illumination of the manipulation region of the endoscope 10, which is practically harmless.

Here, the array-shaped light source 20 is connected to the proximal end 14 of the optical fibre bundle 11 in such a way that these are adhesively bonded to one another in a positionally secured manner and, as a result thereof, the assignment of the individual-light sources 21 to the individual proximal ends 14 of the optical waveguide fibres 16 is provided in a permanent and unique manner. On the basis of this positionally secured assignment, the assignment table 31 in the memory 32 is realized very reliably and quickly by an automated determination of the assignment function 31 with the aid of an appropriate device. An example for such an arrangement for determining an assignment table 31 is depicted schematically in FIG. 4.

The array-shaped light source 20 is connected over the whole area thereof to the optical fibre bundle 11 with the aid of an optically transparent adhesive element 22 in such a way that the light emitted by the individual-light sources 21 of the light source 20 is coupled directly into the proximal end surface 14 of the contiguous bundle 12 of the optical fibre bundle 11. One or more optical units 23 may be arranged between individual-light sources 21 and the proximal end 14. The adhesively bonded module provides a pre-manufactured light transmission module which is installed into an endoscope 10 according to the invention in the pre-assembled state. The optical fibre bundle 11 has been coupled to the light source 20 in such a way that an individual-light source 21 couples light exclusively, or substantially exclusively, into only one individual optical fibre 16. This optical fibre 16 transmits the coupled-in light from the proximal end 14 to the distal end 15 of the optical waveguide fibre 16. There, the light emerges from the end surface and can be logged with the aid of photodiodes 40, which are respectively directed to a distal end of a partial bundle 13 of the optical fibre bundle 11. Each photodiode 40 is assigned to a single partial bundle 13.

In order to establish the assignment function or the assignment table, there is a sequential activation of individual-light source 21 by individual-light source 21 and there is respective determination as to which photo-sensor detects an increase in brightness such that the assignment of a specific individual-light source 21 to an optical fibre 16, and hence to a partial bundle 13, is determined and logged, and stored in a memory such as e.g. the memory 42. As a result of the sequential actuation of all individual-light sources 21 of the array-shaped light source 20 by the controller 41, it is possible to determine and store the assignment function, which is embodied as assignment table 43, 31, for the whole array of individual-light sources. Here, an identification of the respective partial bundle 13, for example in the form of numbering 1, 2, 3, 4, is respectively used in the assignment table 43, 31. If no increase in the brightness is sensed by any of the photodiodes 40 when activating an individual-light source 21 of the array-shaped light source 20, an entry representing a defect, e.g. 0, is written. By way of example, a defect may be caused by a defective individual-light source 21, by a break in the optical waveguide fibre or by dirtying, for example in the region of the adhesive connection 22. According to the invention, the individual-light source 21 which is assigned to a cell of the assignment table 31 with the value 0 is not actuated by the control arrangement 30 during the operation of the endoscope 10 such that no thermal or energetic load on the system emerges from this individual-light source 21 either.

The method according to the invention for determining an assignment function for such an endoscope described in a manner according to the invention provides a very reliable and safe and simple determination of the assignment function which enables a very efficient and reliable operation of an endoscope according to the invention.

The invention claimed is:

1. An endoscope, exoscope or microscope, comprising
an optical fibre bundle for transmitting light from the proximal end thereof to the distal end thereof,
said optical fibre bundle having a contiguous bundle at the proximal end and a plurality of partial bundles at the distal end, the plurality of partial bundles each separated from one another and having a plurality of optical fibres,
a light source for coupling light into a proximal end of the optical fibre bundle and comprising a multiplicity of individual-light sources arranged in an array-like manner, and comprising a control unit for actuating the light source,
wherein the multiplicity of individual-light sources are individually actuatable,
the control unit is adapted for actuating the individual-light sources using an assignment function, which represents the assignment of a proximal fibre end to a partial bundle, and
the proximal ends of the fibres assigned to one partial bundle are arranged on a surface in such a way that therebetween proximal ends of fibres assigned to a different partial bundle are arranged.

2. The endoscope, exoscope or microscope as claimed in claim 1, wherein the light source includes an array of light emitting diodes, or semiconductor lasers, or optical waveguide fibre ends.

3. The endoscope, exoscope or microscope as claimed in claim 1, wherein the form and/or the size of the proximal end of the optical fibre bundle corresponds to the light source.

4. The endoscope, exoscope or microscope as claimed in claim 1, wherein the form and/or the size of one fibre end at the proximal end of the optical fibre bundle corresponds to the form and/or the size of the assigned individual-light sources.

5. The endoscope, exoscope or microscope as claimed in claim 1, wherein individual-light sources couple light directly into a single fibre.

6. The endoscope, exoscope or microscope as claimed in claim 1, wherein one or more optical units are arranged between individual-light sources and the proximal end of the optical fibre bundle.

7. The endoscope, exoscope or microscope as claimed in claim 1, wherein the proximal end of the optical fibre bundle is connected to the light source in a positionally secured manner.

8. The endoscope, exoscope or microscope as claimed in claim 1, wherein the light source is arranged in the endoscope, exoscope or microscope.

9. The endoscope, exoscope or microscope as claimed in claim 8, wherein the light source is arranged in a handle of the endoscope, exoscope or microscope.

10. The endoscope, exoscope or microscope as claimed in claim 1, wherein the light source is embodied in a manner detached from the endoscope, exoscope or microscope and connected by means of an optical fibre cable for supplying light.

11. The endoscope, exoscope or microscope as claimed in claim 10, wherein the assignment function is configured in a manner selectable as a function of the detached light source.

12. The endoscope, exoscope or microscope as claimed in claim 10, wherein setting the position of the light source in relation to the proximal end of the optical fibre bundle is unambiguous.

13. The endoscope, exoscope or microscope as claimed in claim 1, wherein the partial bundles at a distal end of the endoscope point in different directions.

14. The endoscope, exoscope or microscope as claimed in claim 1, wherein the control unit for actuating the light source is additionally suitable for actuating the light source with a predetermined illumination profile.

15. The endoscope, exoscope or microscope as claimed in claim 1, wherein all or some of the individual-light sources are activated selectively and an optical detector is used to log which partial bundle at the distal end of the optical fibre bundle emits light and this is stored as an assignment function.

16. The endoscope, exoscope or microscope as claimed in claim 1, further comprising a plurality of light openings at the distal end of the endoscope, each one of the plurality of partial bundles arranged into each one of the plurality of light openings for transmitting light therethrough.

17. The endoscope, exoscope or microscope as claimed in claim 1, wherein the assignment function is selected from a plurality of assignment functions that are stored in a memory, each of the plurality of assignment functions relating to a different position or orientation of the light source.

18. A method for illuminating a manipulation region of an endoscope, exoscope or microscope, in which light is transmitted by means of an optical fibre bundle from a proximal end, which has a contiguous bundle, to a distal end, which has a plurality of partial bundles, the plurality of partial bundles each separated from one another and having a plurality of optical fibres,
wherein light is coupled into the one proximal end of the optical fibre bundle by means of a light source comprising a multiplicity of individual-light sources which are arranged in an array-shaped manner and which are individually actuatable, and
wherein the individually actuatable individual-light sources of the light source are actuated with the aid of a control unit using an assignment function which represents the assignment of a proximal fibre end of the optical fibre bundle to a partial bundle.

19. The method for illuminating a manipulation region of an endoscope, exoscope or microscope as claimed in claim 18, wherein the identity of the light source and/or the position in relation to the proximal end of the optical fibre bundle is logged and an assignment function for actuating the individually actuatable individual-light sources of the light source is selected.

* * * * *